United States Patent
Yamamori et al.

(10) Patent No.: US 9,839,398 B2
(45) Date of Patent: Dec. 12, 2017

(54) DISPLAY DEVICE AND METHOD FOR DISPLAYING

(71) Applicant: NIHON KOHDEN CORPORATION, Tokyo (JP)

(72) Inventors: Shinji Yamamori, Tokyo (JP); Toshiki Aoki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 430 days.

(21) Appl. No.: 14/559,578

(22) Filed: Dec. 3, 2014

(65) Prior Publication Data

US 2015/0157241 A1 Jun. 11, 2015

(30) Foreign Application Priority Data

Dec. 5, 2013 (JP) ................................. 2013-252472

(51) Int. Cl.
| | | |
|---|---|---|
| *A61B 5/091* | (2006.01) | |
| *A61B 5/00* | (2006.01) | |
| *A61B 5/083* | (2006.01) | |
| *A61B 5/08* | (2006.01) | |

(52) U.S. Cl.
CPC ............ *A61B 5/742* (2013.01); *A61B 5/0836* (2013.01); *A61B 5/091* (2013.01); *A61B 5/0826* (2013.01)

(58) Field of Classification Search
CPC ..... A61B 5/0826; A61B 5/0836; A61B 5/091; A61B 5/742
USPC ........................................ 600/529-543, 484
See application file for complete search history.

(56) References Cited

U.S. PATENT DOCUMENTS

| | | | | |
|---|---|---|---|---|
| 4,706,664 A | * | 11/1987 | Snook ................... | A61M 16/00 128/204.23 |
| 4,777,962 A | * | 10/1988 | Watson ................ | A61B 5/7264 600/529 |
| 4,932,402 A | * | 6/1990 | Snook ................... | A61M 16/00 128/204.23 |
| 4,938,212 A | * | 7/1990 | Snook ................... | A61M 16/00 128/205.24 |

(Continued)

FOREIGN PATENT DOCUMENTS

JP 2011-045592 3/2011

*Primary Examiner* — Navin Natnithithadha
(74) *Attorney, Agent, or Firm* — Konomi Takeshita

(57) ABSTRACT

The present invention provides a device for displaying respiratory conditions of a subject on a monitor having a first parameter acquisition unit (11) for acquiring a first respiration parameter representing a respiratory condition of the subject; a second parameter acquisition unit (12) for acquiring a second respiration parameter representing a respiratory condition of the subject, said second respiration parameter differing from said first respiration parameter; and a display controlling unit (13) for displaying, on the monitor, a chart representing a relationship between the first respiration parameter acquired by said first parameter acquisition unit and the second respiration parameter acquired by said second parameter acquisition unit; wherein the chart represents the relationship between the first respiration parameter and the second respiration parameter in each respiration cycle, and a plurality of charts for preceding respiration cycles and charts for subsequent respiration cycles are displayed so as to adjoin one another successively in a prescribed direction.

16 Claims, 5 Drawing Sheets

(56) References Cited

U.S. PATENT DOCUMENTS

| | | | | |
|---|---|---|---|---|
| 5,167,610 | A * | 12/1992 | Kitado | A61M 21/00 128/905 |
| 5,875,777 | A * | 3/1999 | Eriksson | A61M 16/0051 128/204.21 |
| 6,819,957 | B1 * | 11/2004 | Le | A61N 1/0452 128/905 |
| 7,896,813 | B2 * | 3/2011 | Sowelam | A61B 5/08 600/484 |
| 8,398,560 | B2 * | 3/2013 | Elser | A61B 5/08 600/534 |
| 8,418,693 | B2 * | 4/2013 | Kaestle | A61B 5/0833 128/204.18 |
| 2010/0101577 | A1 * | 4/2010 | Kaestle | A61B 5/0836 128/204.22 |
| 2012/0204875 | A1 * | 8/2012 | Brazy | A61M 16/0051 128/204.22 |
| 2013/0165806 | A1 * | 6/2013 | Wondka | A61B 5/0816 600/532 |
| 2013/0217980 | A1 * | 8/2013 | Elser | A61B 5/0059 600/301 |
| 2014/0032241 | A1 * | 1/2014 | Coffeng | G06F 19/3406 705/3 |

* cited by examiner (a)

(b)

(a)

(b)

DISPLAY DEVICE AND METHOD FOR DISPLAYING

CROSS REFERENCE TO RELATED APPLICATIONS

This application claims priority under 35 U.S.C. 119 based upon Japanese Patent Application Serial No. 2013-252472, filed on Dec. 5, 2013. The entire disclosures of the aforesaid applications are incorporated herein by reference.

FIELD OF THE INVENTION

The present invention pertains to a device and method for displaying the relationship amongst a plurality of respiration parameters acquired from a patient.

BACKGROUND OF THE INVENTION

Amongst devices of the same variety as the present device, devices which mark on a first coordinate axis the carbon dioxide concentration in air breathed by a subject, and mark on a second coordinate axis ventilation volume from the subject breathing, and display a pattern representing the relationship between the carbon dioxide concentration and ventilation volume on a coordinate plane formed from the first coordinate axis and the second coordinate axis, are well-known (for example, Japanese Laid-Open Patent Publication No. 2011-45592, hereafter referred as Patent Document 1). From such devices, the condition of the lungs of a subject can be diagnosed from the shape of the pattern displayed.

The abovementioned pattern representing the relationship between carbon dioxide concentration and ventilation volume form a hysteresis loop which closes with each respiration cycle from the subject (a cycle consisting of one exhalation and one inhalation). Accordingly, in order to display said relationship of the next respiration cycle, it is necessary to erase the hysteresis loop which was originally formed for the display of a new hysteresis loop to begin, or a new hysteresis loop has to be displayed by overwriting the hysteresis loop which was originally formed. Therefore, it is difficult to ascertain trends for said relationship (changes in each respiration cycle), and there is a burden being placed on medical practitioners.

Considering the above situation, the purpose of the present invention is to provide a technique which reduces the burden on medical practitioners by displaying the relationship amongst a plurality of respiration parameters.

SUMMARY OF THE INVENTION

In order to attain the above object, according to a first principal aspect of the present invention, there is provided a device for displaying respiratory conditions of a subject on a monitor comprising: a first parameter acquisition unit for acquiring a first respiration parameter representing a respiratory condition of the subject; a second parameter acquisition unit for acquiring a second respiration parameter representing a respiratory condition of the subject, said second respiration parameter differing from said first respiration parameter; and a display controlling unit for displaying, on the monitor, a chart representing a relationship between the first respiration parameter acquired by said first parameter acquisition unit and the second respiration parameter acquired by said second parameter acquisition unit; wherein the chart represents the relationship between the first respiration parameter and the second respiration parameter in each respiration cycle, and a plurality of charts for preceding respiration cycles and charts for subsequent respiration cycles are displayed so as to adjoin one another successively in a prescribed direction.

According to one embodiment of the present invention, the device further comprises: a detector for detecting an exhalation interval and inhalation interval from the subject, wherein the chart of each respiration cycle is displayed such that a chart that displays the relationship between the first respiration parameter and the second respiration parameter in the exhalation interval, and a chart that displays the relationship between the first respiration parameter and the second respiration parameter in the inhalation interval are displayed so as to adjoin one another successively. In this embodiment, it is desirable that a direction in which a value of the first respiration parameter changes within a chart in the exhalation interval is arranged along a direction in which the plurality of charts are adjoined, and said direction is arranged so as to be in an opposite direction from a direction in which a value of the first respiration parameter changes within a chart in the inhalation interval.

According to another embodiment, the device further comprises: a timer for timing each duration of each respiration cycle, wherein the display controlling unit displays information corresponding to the duration of each respiration cycle in each chart. In this embodiment, it is preferable the display controlling unit, in cases in which the duration exceeds a prescribed threshold, modifies a display mode of the chart corresponding to said duration. Further in this embodiment, it is desirable that the threshold is a value that determines that the subject is in a state of apnea.

According to yet another embodiment, the prescribed direction is toward the right in a horizontal direction.

According to still another embodiment, the first respiration parameter and the second respiration parameter are two parameters selected from a carbon dioxide concentration in the air breathed by the subject, a ventilation volume from the subject breathing, and a respiratory pressure from the subject.

Furthermore, according to second principal aspect of the present invention, there is provided a method for displaying, on a monitor, respiratory conditions of a subject comprising steps of: a first parameter acquisition step for acquiring a first parameter representing a respiratory conditions of the subject; a second parameter acquisition step for acquiring a second respiration parameter representing a respiratory conditions of the subject, said second respiration parameter differing from said first respiration parameter; and a display controlling step for displaying, on the monitor, a chart representing a relationship between the first respiration parameter acquired by said first parameter acquisition step, and the second respiration parameter acquired by said second parameter acquisition step; wherein the chart represents the relationship between the first respiration parameter and the second respiration parameter in each respiration cycle, and a plurality of charts for preceding respiration cycles and charts for subsequent respiration cycles are displayed so as to adjoin one another successively in a prescribed direction.

Other features and advantages of the present invention will become apparent from the following detailed description, taken in conjunction with the accompanying drawings, which illustrate, by way of example, the principles of the invention.

DETAILED DESCRIPTION OF THE INVENTION

An embodiment of the present invention will be explained in detail below referencing the attached drawings.

Figure 1:
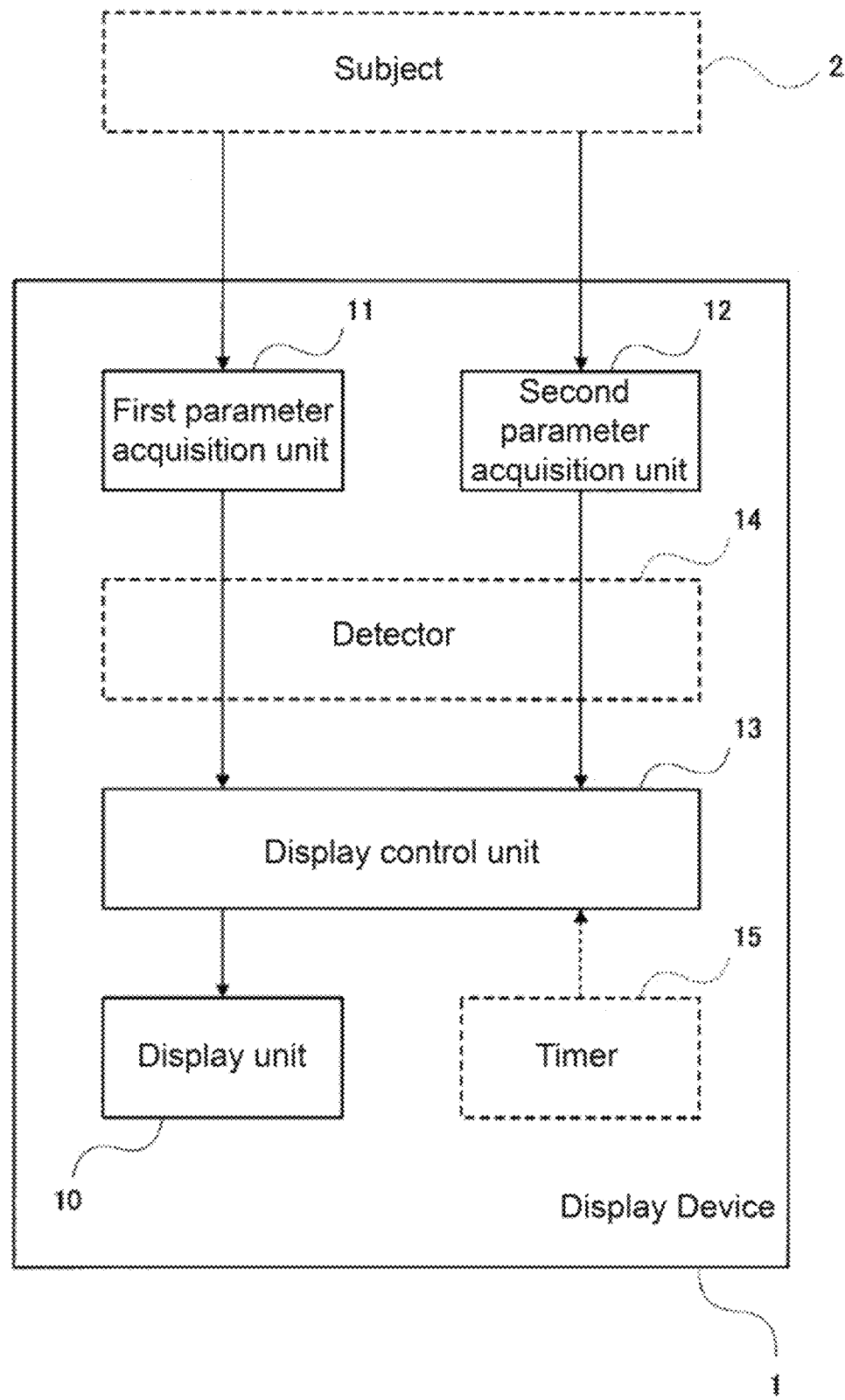
FIG. 1 is a functional block diagram representing a configuration of a display device (1) according to one embodiment of the present invention.

FIG. 1 is a functional block diagram representing a configuration of a display device (1) according to one embodiment of the present invention. The display device (1) may be a capnometer, for example. The display device (1) comprises a display unit (10), a first parameter acquisition unit (11), a second parameter acquisition unit (12), and a display controlling unit (13).

The display unit (10) has a screen upon which information is able to be transmitted to medical practitioners visually. The term "screen" is also meant to include the application window which is displayed on the display.

The first parameter acquisition unit (11) acquires a first respiration parameter from a subject (2). The ventilation volume from the subject (2) breathing can be given as an example of a first respiration parameter. In such cases, the first parameter acquisition unit (11) would be configured as a flow sensor, for example.

The second parameter acquisition unit (12) acquires a second respiration parameter from the subject (2). The carbon dioxide concentration in the air breathed by the subject (2) can be given as an example of a second respiration parameter. In such cases, the second parameter acquisition unit (12) would be configured as a respiratory gas sensor, for example.

The display controlling unit (13) displays, on the display unit (10), a chart representing the relationship between the first respiration parameter and the second respiration parameter, on the basis of the first respiration parameter acquired by the first parameter acquisition unit (11), and the second respiration parameter acquired by the second parameter acquisition unit (12).

Figure 2A:
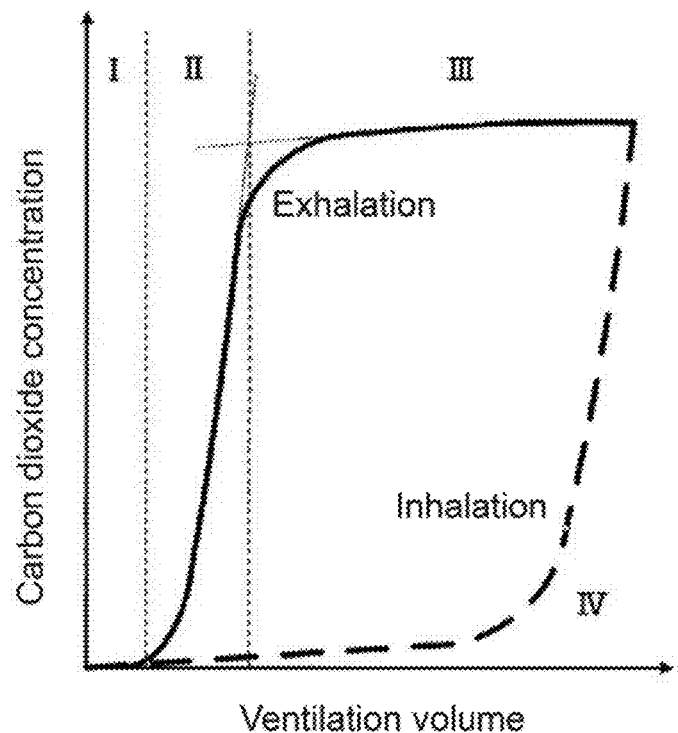
FIGS. 2A and 2B are examples of charts displayed in the display unit of the display device according to one embodiment of the present invention.

A $CO_2$-Volume curve (CV curve), which is one example of such a chart, is illustrated in FIG. 2A. The display unit (10) contains the coordinate plane formed from the first coordinate axis and the second coordinate axis. The horizontal axis, which is an example of the first coordinate axis, represents ventilation volume (Volume), which is an example of the first respiratory parameter. The vertical axis, which is an example of the second coordinate axis, represents carbon dioxide concentration, which is an example of the second respiratory parameter. The display controlling unit (13) plots, on the coordinate plane, ventilation volume and carbon dioxide concentration values acquired at the same point in time.

A hysteresis loop shaped CV curve is formed from each respiration cycle, consisting of one exhalation and one inhalation, as the transitions in plot positions which accompany breathing are recorded. The solid line represents transitions in plot positions during exhalation, and the dashed line represents transitions in plot positions during inhalation.

The characters I-IV in the figure indicate that each region within the chart corresponds to Phase I-IV in the capnogram. Phase I consists of deadspace gas emissions, and increases in carbon dioxide concentration rarely occur. Phase II consists of exhaled gas emissions at the peripheral bronchial tube level, and abrupt increases in carbon dioxide concentration have been confirmed. Phase III consists of exhaled gas emissions at the alveolar level, and increases in carbon dioxide concentration accompanying increased ventilation volume are moderate. Phase IV consists of inhalation. It is known that the condition of the lungs of a subject can be diagnosed from the gradient of the plot trajectory in Phases II and III.

Figure 2B:
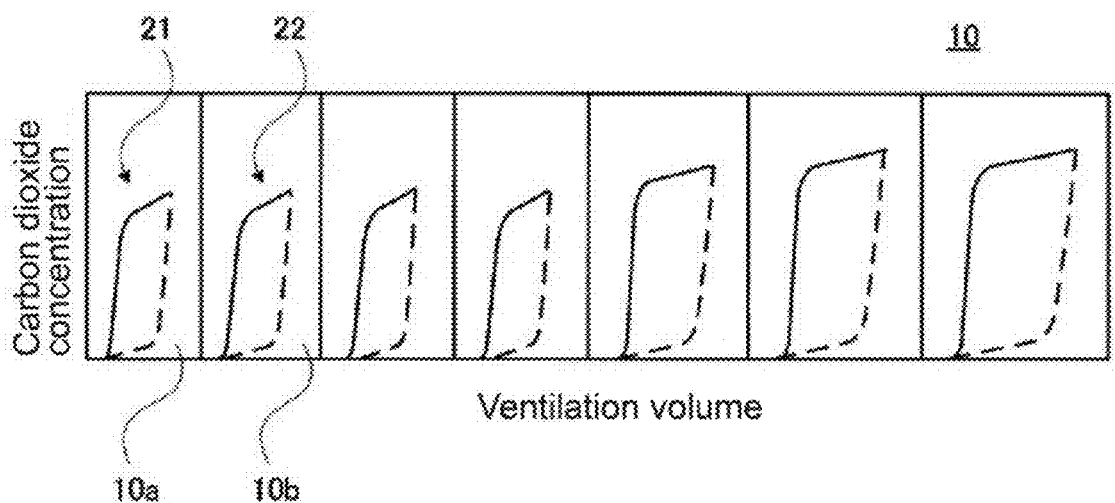

As illustrated in FIG. 2B, the display controlling unit (13) aligns and displays a plurality of chart displaying regions in the horizontal direction of the display unit (10). The CV curve for each respiration cycle is displayed in each of the plurality of chart displaying regions. The chart displaying region (10a) (example of a first displaying region) positioned on the leftmost side in the figure, and the adjoining chart displaying region (10b) (example of a second displaying region) on the right side thereof (example of a prescribed direction) will be used as examples, and explained in detail below.

The horizontal axis and vertical axis in the chart displaying region (10a) represent the ventilation volume and carbon dioxide concentration, respectively, in a respiration cycle (first respiration cycle). The horizontal axis and vertical axis in the chart displaying region (10b) represent the ventilation volume and carbon dioxide concentration, respectively, in the respiration cycle subsequent to the first respiration cycle (second respiration cycle). The CV curve (21) of the first respiration cycle is displayed in the chart displaying region (10a). The CV curve (22) of the second respiration cycle is displayed in the chart displaying region (10b).

Likewise, the CV curves obtained in each subsequent respiration cycle are displayed so as to adjoin the right side successively. From such a configuration, medical practitioners can easily ascertain CV curve trends (changes in each respiration cycle) representing the respiratory conditions of a subject. Accordingly, the burden placed on medical practitioners can be reduced.

As illustrated in FIG. 1, the display device (1) may be configured to further comprise a detector (14). The detector (14) detects the exhalation interval and the inhalation interval from the subject (2), on the basis of the value of the first respiration parameter acquired by the first parameter acquisition unit (11) and the value of the second respiration parameter acquired by the second parameter acquisition unit (12).

For example, a transition from exhalation to inhalation may be verified by means of the ventilation volume from the patient detected by the flow sensor changing from increasing to decreasing. Moreover, a transition from exhalation to inhalation may be verified by means of the carbon dioxide concentration detected by the respiratory gas sensor changing from increasing to decreasing. Furthermore, a transition from inhalation to exhalation, i.e. a transition to the next respiratory cycle, may be verified by means of such values changing from decreasing to increasing. The detector (14) detects transitions from an exhalation interval to an inhalation interval, and transitions from an inhalation interval to an exhalation interval (transitions to the next respiratory cycle) on the basis of at least one of the acquired ventilation volume and carbon dioxide concentration.

Figure 3A:
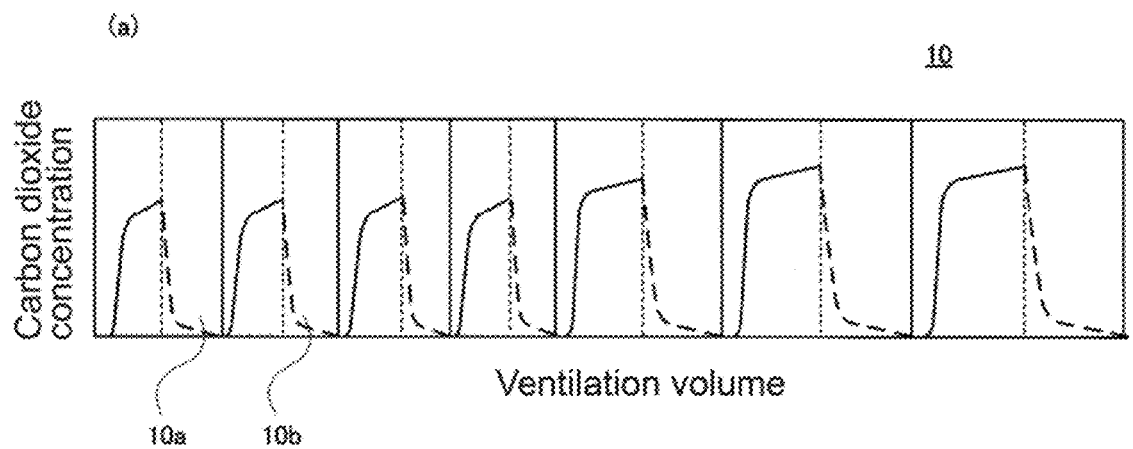
FIGS. 3A and 3B are another example of charts displayed in the display unit of the display device.

In such cases, the display controlling unit (13) displays, on the display unit (10), a chart representing the relationship between the first respiration parameter and the second respiration parameter on the basis of detection results from the detector (14). FIG. 3A illustrates an example of such a chart.

Figure 3B:
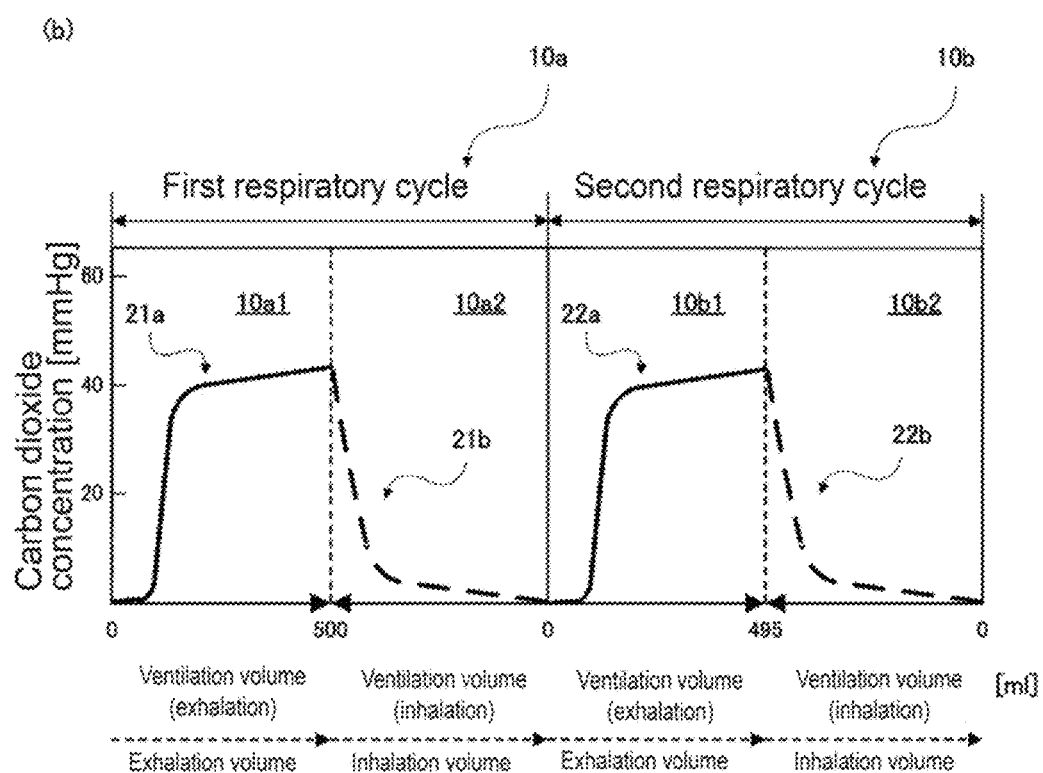

As in the chart illustrated in FIG. 2B, the display controlling unit (13) aligns and displays a plurality of regions in the horizontal direction of the display unit (10). The CV curve for each respiration cycle is displayed in each of the plurality of regions. However, in the example in FIG. 3A, the display mode for the CV curve differs from the example illustrated in FIG. 2B. The chart displaying region (10a) positioned on the leftmost side of the figure, and the adjoining chart displaying region (10b) on the right side thereof are enlarged and illustrated in FIG. 3B, and will be explained in detail below.

The display controlling unit (13) displays a CV curve corresponding to an exhalation interval, and a CV curve corresponding to an inhalation interval so as to adjoin in the horizontal direction in both the chart displaying region (10a) (example of a first region) and the chart displaying region (10b) (example of a second region).

Specifically, at the timing of a transition from an exhalation interval to an inhalation interval detected by the detector (14), the display controlling unit (13) divides the chart displaying region (10a) into sub-regions ((10a1) and (10a2)) aligned in the horizontal direction. Next, the display controlling unit (13) displays, in the sub-region (10a1), a CV curve (21a) corresponding to the exhalation interval of the first respiration cycle, and displays, in the sub-region (10a2), a CV curve (21b) corresponding to the inhalation interval of the first respiration cycle. The CV curve (21b) adjoins the CV curve (21a) on the right side thereof.

Accordingly, the value of the ventilation volume in the left-side sub-region (10a1) increases toward the right side, while the value of the ventilation volume in the right-side sub-region (10a2) decreases toward the right side. The horizontal axis in the left-side sub-region (10a1) is interpreted as representing exhalation volume and the horizontal axis in the right-side sub-region (10a2) is interpreted as representing inhalation volume. However, since the value of ventilation volume differs with each respiration cycle, the length of the horizontal axis changes in each respiration cycle.

Likewise, at the timing of a transition from an exhalation interval to an inhalation interval detected by the detector (14), the display controlling unit (13) divides the chart displaying region (10b) into sub-regions ((10b1) and (10b2)) aligned in the horizontal direction. Next, the display controlling unit (13) displays, in the sub-region (10b1) on the left side, a CV curve (22a) corresponding to the exhalation interval of the second respiration cycle and displays, in the sub-region (10b2) on the right side, a CV curve (22b) corresponding to the inhalation interval of the second respiration cycle. The CV curve (22a) adjoins the CV curve (21b) on the right side thereof, and the CV curve (22b) adjoins the CV curve (22a) on the right side thereof.

Furthermore, the CV curve corresponding to the exhalation interval and the CV curve corresponding to the inhalation interval obtained in each subsequent respiration cycle are displayed so as to adjoin the right side successively. As a result, medical practitioners are presented with a chart such as the one illustrated in FIG. 3A.

From such a display mode, the displayed CV curves resemble capnograms (waveforms representing changes over time of carbon dioxide concentration and the like) which medical practitioners are ordinarily accustomed to viewing, whereby medical practitioners can more intuitively ascertain CV curve trends (changes in each respiration cycle) representing the respiratory conditions of a subject. Accordingly, the burden placed on medical practitioners can be reduced.

As illustrated in FIG. 1, the display device (1) may also be configured to comprise a timer (15). The timer (15) times the duration of each respiration cycle from the subject (2). In performing timing, the bounds of each respiration cycle can be defined as the point in time at which at least one of the value of the first respiration parameter acquired by the first parameter acquisition unit (11) or the value of the second respiration parameter acquired by the second parameter acquisition unit (12) reaches an initial value. Moreover, the detection results from the detector (14) for the exhalation interval and the inhalation interval may be used.

In such cases, the display controlling unit (13) displays, in each chart displaying region aligned in the horizontal direction, information corresponding to the duration of the respiration cycle timed by the timer (15). Moreover, for cases in which the timed duration exceeds a prescribed threshold, the display controlling unit (13) modifies the display mode of the chart corresponding to said duration. Specific examples of display modes are illustrated in FIGS. 4A-4C and FIGS. 5A and 5B. In each example, chart displaying regions (10a-10d) which correspond to four respiration cycles are aligned in the horizontal direction and displayed on the display unit (10).

Figure 4A:
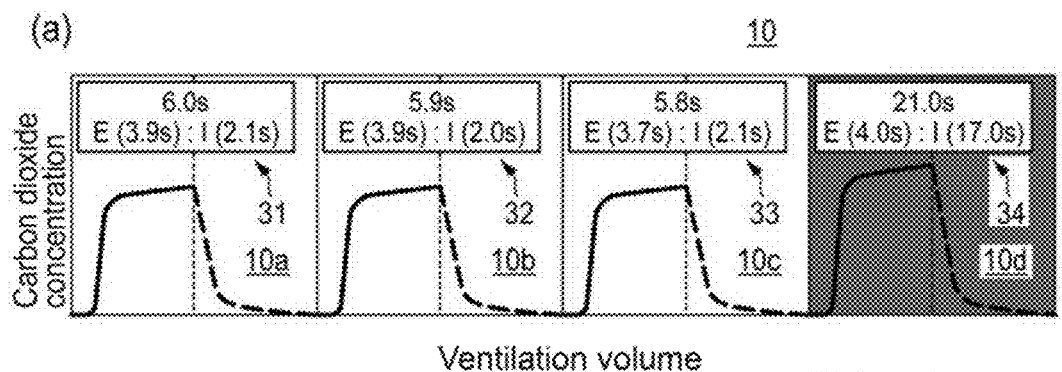
FIGS. 4A-4C are another example of charts displayed in the display unit of the display device.
Figure 4B:
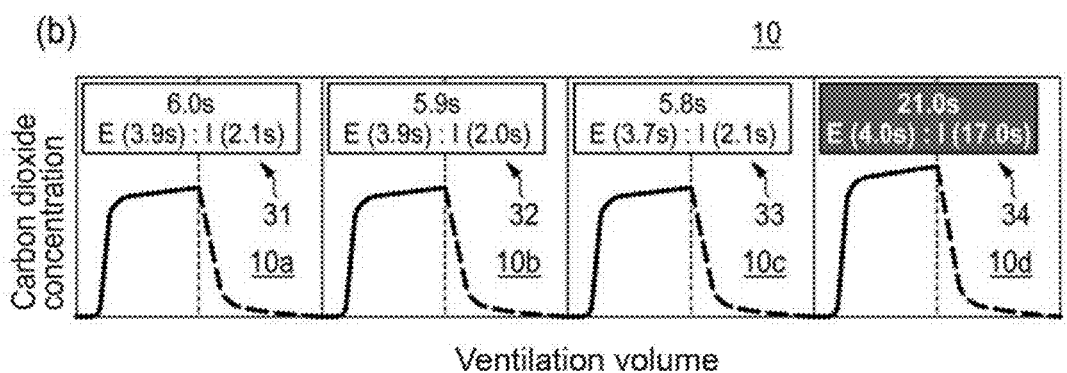

In the examples illustrated in FIGS. 4A and 4B, indices (31-34) which represent the timed results from the timer (15) as numerical values are displayed within the chart displaying regions (10a-10d), respectively. For example, the index (32) displayed in the chart displaying region (10b) is a respiration cycle duration of 5.9 seconds, from which the exhalation interval is indicated as 3.9 seconds and the inhalation interval is 2.0 seconds.

In the example illustrated in FIG. 4A and the example illustrated in FIG. 4B, the display mode for cases in which the duration of the timed respiration cycle exceeds a prescribed threshold differs. In said examples, the prescribed threshold is set at 20 seconds. The respiration cycle duration corresponding to the chart displaying region (10d) is 21 seconds, and is determined to exceed said threshold. The display controlling unit (13) modifies the display mode of the chart displaying region (10d) which corresponds to said duration.

In the example illustrated in FIG. 4A, the color of the entire chart displaying region (10d) is modified so as to differ from the other chart displaying regions (10a-10c). In the example illustrated in FIG. 4B, the color of the index (34) displayed in the chart displaying region (10d) is modified so as to differ from the other indices (31-33).

Figure 4C:
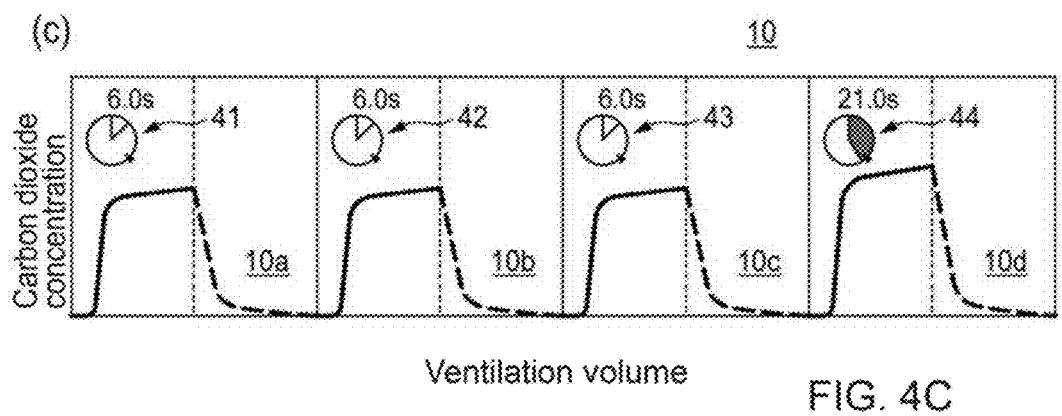

In the example illustrated in FIG. 4C, indices (41-44) which represent the timed results from the timer (15) as pie charts are displayed within the chart displaying regions (10a-10d), respectively. For each index (41-44), the timed results are indicated as numerical values above the pie charts. Moreover, the pie charts in each index (41-44) are provided with a mark that represents the prescribed threshold.

In said example, the prescribed threshold is set at 20 seconds. The respiration cycle duration corresponding to the chart displaying region (10d) is 21 seconds, and is determined to exceed said threshold. The display controlling unit (13) modifies the display mode of the chart displaying region (10d) which corresponds to said duration. Specifically, the color of one portion of the pie chart in the index (44) is modified so as to differ from the other indices (41-43).

Figure 5A:
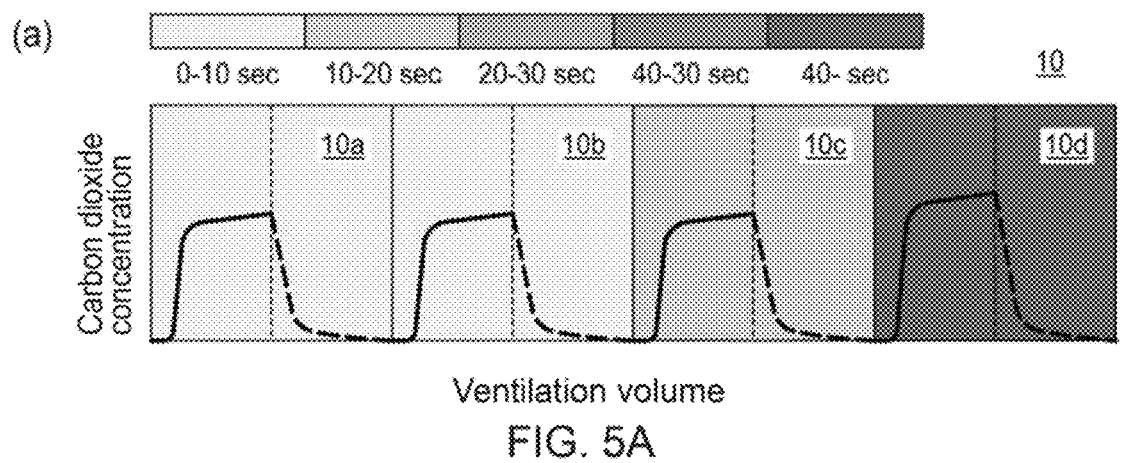
FIGS. 5A and 5B are another example of charts displayed in the display unit of the display device.

In the example illustrated in FIG. 5A, the color of each chart displaying region (10a-10d) is modified in accordance with information corresponding to the duration of the respiration cycle timed by the timer (15). In said example, cases in which the duration is less than 10 seconds are displayed in blue, cases that are 10 seconds or more but less than 20 seconds are green, cases that are 20 seconds or more but less than 30 seconds are yellow, cases that are 30 seconds or more but less than 40 seconds are orange, and cases that are 40 seconds or more are red. As above, the duration threshold is set at 20 seconds. Chart displaying regions for respiration cycle durations which exceed 20 seconds are displayed in more attention-drawing colors.

Specifically, since the duration of the respiration cycles corresponding to the chart displaying regions ((10a) and (10b)) are less than 10 seconds, said regions are displayed in blue. Since the duration of the respiration cycle corresponding to the chart displaying region (10c) is 10 seconds or more but less than 20 seconds, said region is displayed in green. Since the duration of the respiration cycle corresponding to the chart displaying region (10d) is 40 seconds or more, said region is displayed in red.

Figure 5B:
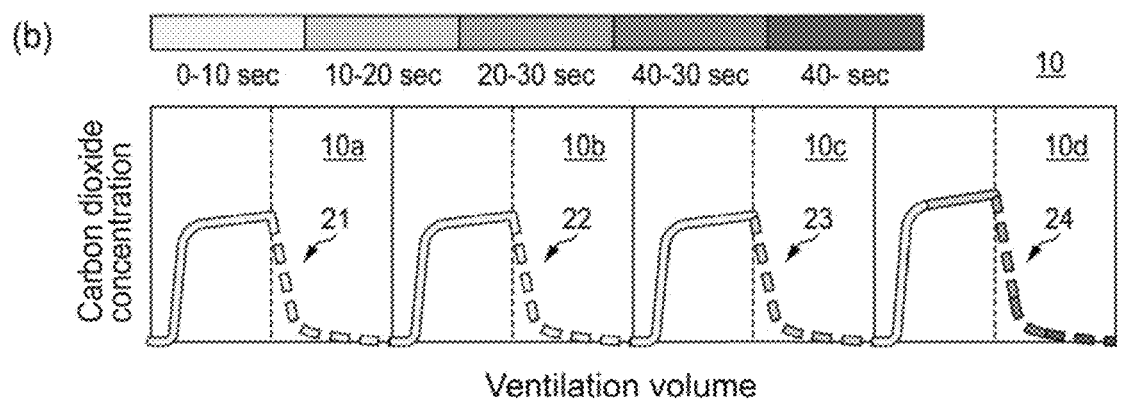

In the example illustrated in FIG. 5B, the color of each CV curve (21-24) displayed in the chart displaying regions (10a-10d), in particular, is modified in accordance with information corresponding to the duration of the respiration cycle timed by the timer (15). The relationship between duration and color is the same as the example illustrated in FIG. 5A.

Specifically, since the duration of the respiration cycles corresponding to the chart displaying regions ((10a) and (10b)) are less than 10 seconds, the entire CV curves ((21) and (22)) are displayed in blue. Since the duration of the respiration cycle corresponding to the chart displaying region (10c) is 10 seconds or more but less than 20 seconds, the CV curve (23) changes colors midway from blue to green. Since the duration of the respiration cycle corresponding to the chart displaying region (10d) is 40 seconds or more, the CV curve (24) changes colors midway from blue, to green, to yellow, to orange, to red. Medical practitioners can easily ascertain which portion of the CV curve belongs to which duration segment.

The CV curves displayed by the display controlling unit (13), in particular, do not contain information on exact values for the duration of respiration cycles. Namely, in the charts displayed on the display unit (10), although it is intelligible that the data more toward the right is newer temporally, since the horizontal axis ultimately represents ventilation volume, the duration of each respiration cycle is not precisely intelligible. However, respiration cycle duration is an important parameter for ascertaining respiratory disorders and the like in a subject.

From the configuration represented in each of the above-mentioned examples, information indicating the duration of each respiration cycle is displayed within each chart displaying region. Therefore, medical practitioners can ascertain not only CV curve trends (changes in each respiration cycle) representing the respiratory conditions of a subject, but can also easily ascertain the duration of respiration cycles which is an important parameter. Accordingly, the burden being placed on medical practitioners can be reduced.

The fact that the duration of a timed respiration cycle exceeds a threshold may suggest a state in which some sort of respiratory disorder is occurring in the subject (2). From the abovementioned configuration, the respiration cycle in which such a state is considered to have occurred may be specified and reported. Medical practitioners, receiving said report, can easily ascertain such a state. Accordingly, the burden being placed on medical practitioners can be reduced.

For example, the threshold may be set at a value that determines that the subject (2) is in a state of apnea.

In such cases, medical practitioners, receiving the abovementioned report, can take prompt action against the subject (2). Accordingly, the burden being placed on medical practitioners can be reduced.

It is to be understood that the embodiment heretofore described is no more than one embodiment of the present invention, and that various changes and modifications can be made without departing from the scope and spirit of the present invention . . . .

For example, the display of information corresponding to the respiration cycle duration explained in reference to FIG. 4 and FIG. 5 may also be applied to the CV curve display mode explained in reference to FIG. 2.

In the abovementioned embodiments, ventilation volume is selected as the first respiration parameter and carbon dioxide concentration is selected as the second respiration parameter. However, the first respiration parameter and the second respiration parameter may be arbitrarily defined within the limitation of two parameters selected amongst ventilation volume from a subject breathing, carbon dioxide concentration from the subject's respiration, and respiratory pressure from the subject.

In the abovementioned embodiments, each chart displaying region is displayed on the display unit (10) so as to align in the horizontal direction, and newer charts are positioned so as to adjoin older charts on the right side thereof. From such a configuration, medical practitioners can intuitively ascertain respiratory condition trends from a subject, since the display mode is the same as ordinary biological signal display apparatuses. However, each chart displaying region may, for example, be displayed on the display unit (10) so as to align in the vertical direction and newer charts may be positioned so as to adjoin older charts on the bottom side thereof.

In the abovementioned embodiments, the display unit (10), the first parameter acquisition unit (11), the second parameter acquisition unit (12), the display controlling unit (13), the detector (14), and the timer (15) are housed within the same display device (1). However, to the extent that the function of the display device (1) may be realized in entirety, at least one of the abovementioned elements may be placed within a separate device.

What is claimed is:

1. A device for displaying respiratory conditions of a subject on a monitor comprising:
    a first parameter acquisition unit for acquiring a first respiration parameter representing a respiratory condition of the subject;
    a second parameter acquisition unit for acquiring a second respiration parameter representing a respiratory condition of the subject, said second respiration parameter differing from said first respiration parameter; and
    a display controlling unit for displaying, on the monitor, a plurality of charts, each chart representing a relationship between the first respiration parameter acquired by said first parameter acquisition unit and the second respiration parameter acquired by said second parameter acquisition unit for each respiration cycle;
    wherein each chart has a vertical axis and a horizontal axis, and the first respiration parameter is plotted on one of the vertical axis and the horizontal axis and the second respiration parameter is plotted on another one of the vertical axis and the horizontal axis, and wherein the plurality of charts are from preceding respiration cycles and subsequent respiration cycles, and are displayed so as to adjoin one another successively in a prescribed direction.

2. The device of claim 1 further comprising:
a detector for detecting an exhalation interval and inhalation interval from the subject,
wherein the chart of each respiration cycle is displayed such that a chart that displays the relationship between the first respiration parameter and the second respiration parameter in the exhalation interval, and a chart that displays the relationship between the first respiration parameter and the second respiration parameter in the inhalation interval are displayed so as to adjoin one another successively.

3. The device of claim 2 wherein a direction in which a value of the first respiration parameter changes within a chart in the exhalation interval is arranged along a direction in which the plurality of charts are adjoined, and said direction is arranged so as to be in an opposite direction from a direction in which a value of the first respiration parameter changes within a chart in the inhalation interval.

4. The device of claim 1 further comprising:
a timer for timing each duration of each respiration cycle,
wherein the display controlling unit displays information corresponding to the duration of each respiration cycle in each chart.

5. The device of claim 4 wherein the display controlling unit, in cases in which the duration exceeds a prescribed threshold, modifies a display mode of the chart corresponding to said duration.

6. The device of claim 5 wherein the threshold is a value that determines that the subject is in a state of apnea.

7. The device of claim 1 wherein the prescribed direction is toward the right in a horizontal direction.

8. The device of claim 1 wherein the first respiration parameter and the second respiration parameter are two parameters selected from a carbon dioxide concentration in the air breathed by the subject, a ventilation volume from the subject breathing, and a respiratory pressure from the subject.

9. A method for displaying, on a monitor, respiratory conditions of a subject comprising steps of:
a first parameter acquisition step for acquiring a first parameter representing a respiratory conditions of the subject;
a second parameter acquisition step for acquiring a second respiration parameter representing a respiratory conditions of the subject, said second respiration parameter differing from said first respiration parameter; and
a display controlling step for displaying, on the monitor, a plurality of charts, each chart representing a relationship between the first respiration parameter acquired by said first parameter acquisition step and the second respiration parameter acquired by said second parameter acquisition step for each respiration cycle;
wherein each chart has a vertical axis and a horizontal axis, and the first respiration parameter is plotted on one of the vertical axis and the horizontal axis and the second respiration parameter is plotted on another one of the vertical axis and the horizontal axis, and wherein the plurality of charts are from preceding respiration cycles and subsequent respiration cycles, and are displayed so as to adjoin one another successively in a prescribed direction.

10. The method of claim 9 further comprising a step of:
detecting an exhalation interval and inhalation interval from the subject,
wherein the chart of each respiration cycle is displayed such that a chart that displays the relationship between the first respiration parameter and the second respiration parameter in the exhalation interval and a chart that displays the relationship between the first respiration parameter and the second respiration parameter in the inhalation interval are displayed so as to adjoin one another successively.

11. The method of claim 10 wherein a direction in which a value of the first respiration parameter changes within a chart in the exhalation interval is arranged along a direction in which the plurality of charts are adjoined, and said direction is arranged so as to be in an opposite direction from a direction in which a value of the first respiration parameter changes within a chart in the inhalation interval.

12. The method of claim 9 further comprising a step of:
timing each duration of each respiration cycle,
wherein the display controlling step displays information corresponding to the duration of each respiration cycle in each chart.

13. The method of claim 12 wherein the display controlling step, in cases in which the duration exceeds a prescribed threshold, modifies the display mode of the chart corresponding to said duration.

14. The method of claim 13 wherein the threshold is a value that determines that the subject is in a state of apnea.

15. The method of claim 9 wherein the prescribed direction is toward the right in a horizontal direction.

16. The method of claim 9 wherein the first respiration parameter and the second respiration parameter are two parameters selected from carbon dioxide concentration in the air breathed by the subject, ventilation volume from the subject breathing, and respiratory pressure from the subject.

* * * * *